United States Patent [19]
Ratajczak et al.

[11] Patent Number: 5,833,928
[45] Date of Patent: Nov. 10, 1998

[54] SPECIMEN TRANSPORTING AND PROCESSING SYSTEM

[75] Inventors: Janet Ratajczak, McHenry; Donald R. Harreld, Woodstock; Joseph Kus, Ivanhoe; John Posey, McHenry, all of Ill.

[73] Assignee: Sage Products, Inc., Crystal Lake, Ill.

[21] Appl. No.: 567,353

[22] Filed: Nov. 15, 1995

[51] Int. Cl.$^6$ .................................................. B01L 3/00
[52] U.S. Cl. ........................... 422/102; 422/101; 422/61; 422/58; 215/216; 215/221; 220/254; 73/864.41; 73/864.91
[58] Field of Search ..................... 215/216, 221, 215/250, 329, 330, 331; 220/256, 254, 265, 315; 422/58, 61, 101, 102; 73/864.41, 864.91

[56] References Cited

U.S. PATENT DOCUMENTS

| | | | |
|---|---|---|---|
| 3,871,545 | 3/1975 | Bereziat | 215/249 |
| 3,923,185 | 12/1975 | Choksi et al. | 215/253 |
| 4,280,632 | 7/1981 | Yuhara | 215/331 |
| 4,449,640 | 5/1984 | Finkelstein | 220/270 |
| 4,597,501 | 7/1986 | Gueret | 215/330 |
| 4,724,973 | 2/1988 | Shah | 215/246 |
| 4,859,610 | 8/1989 | Maggio | 436/518 |
| 4,940,167 | 7/1990 | Fillmore et al. | 222/153 |
| 5,058,754 | 10/1991 | Hickerson | 215/201 |
| 5,149,506 | 9/1992 | Skiba et al. | 422/102 |
| 5,174,460 | 12/1992 | Minnette | 215/335 |
| 5,238,130 | 8/1993 | Marques et al. | 215/216 |
| 5,431,884 | 7/1995 | McDonough | 422/101 |
| 5,544,770 | 8/1996 | Travisano | 215/230 |

Primary Examiner—Harold Y. Pyon
Attorney, Agent, or Firm—Lee, Mann, Smith, McWilliams, Sweeney & Ohlson

[57] ABSTRACT

A specimen transporting and processing system having a tubular container with a collar threadedly secured at one end and with a cap applied to the collar. The collar is temporarily locked in place on the container by means of an extending tab which is bound in place by a tape strip adhering to the tab and to the container. When the tape strip is removed or broken, the collar can then be unscrewed and removed from the container.

10 Claims, 1 Drawing Sheet

SPECIMEN TRANSPORTING AND PROCESSING SYSTEM

BACKGROUND OF THE INVENTION

This invention relates to collection of specimens, and more particularly to the collection, transporting and processing of a stool sample where the specimen typically is collected by a patient for later diagnostic work.

As explained in U.S. Pat. No. 5,431,884, the disclosure of which is incorporated herein by reference, stool sampling is an important part of modern healthcare. There are a great many ways to collect samples, and the '884 patent discloses what is believed to be a superior process and apparatus for doing so.

While the collecting container of U.S. Pat. No. 5,431,884 is a distinct improvement over collecting systems previously, one problem is inadvertent rotation of the collar holding the filter assembly when it is intended to remove only the sealing cap for the container. In use, normally the patient removes the cap and collects a specimen, while the collar is removed only by a medical diagnostician. If the patient removes more than the cap, the utility of the system can be compromised by alteration.

SUMMARY OF THE INVENTION

The present invention overcomes the identified problem of U.S. Pat. No. 5,431,884 by providing a specimen transporting and processing system having a similar tubular container having an open end. A removable collar is attached to the container at the open end with the collar being threadedly secured to the open end. Means are provided, secured to the collar, for sealing the container at the open end. For temporarily locking the collar in place on the open end when threadedly secured thereto, the collar includes at least one tab extending from the collar adjacent to the container, and means are provided for removably binding the tab to the container.

In accordance with the preferred form of the invention, the means for removably binding the tab to the container comprises a tape strip which adheres to the tab and to adjacent portions of the container. Preferably, the tape strip extends around the entire periphery of the container.

In the preferred form of the invention, a tubular filter is provided, shaped to fit within the container through the open end of the container. The collar is formed with means for gripping the filter, the gripping means comprising an internal annular protrusion in the collar. The filter includes an annular groove which is shaped to engage the protrusion to secure the filter to the removable collar.

In the preferred form of the invention, the means for sealing the container at the open end comprises a threaded cap. A specimen sampling implement is secured to the cap and is shaped to be inserted into the container when the cap is applied thereto.

BRIEF DESCRIPTION OF THE DRAWINGS

The invention is described in greater detail in the following description of an example embodying the best mode of the invention, taken in conjunction with the drawing figures, in which.

DESCRIPTION OF AN EXAMPLE EMBODYING THE BEST MODE OF THE INVENTION

Figure 1:
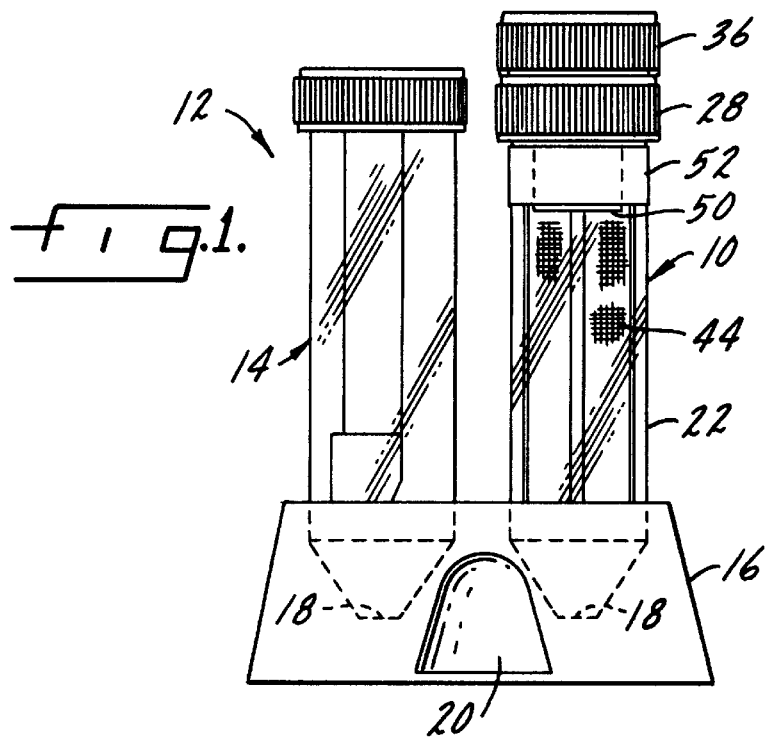
FIG. 1 is an elevational view of a specimen transporting, sampling and processing assembly according to the invention.

A specimen transporting and processing system according to the invention is shown generally at 10 in the drawing figures. The specimen transporting and processing system 10 can be used alone, or can be part of a specimen transporting, sampling and processing assembly as shown at 12 in FIG. 1, where the system 10 and a second container 14 are provided in a holder 16 which retains the two containers in an upright orientation. As explained in greater detail in incorporated U.S. Pat. No. 5,431,884, the holder 16 has a pair of cavities 18 for holding the system 10 and the second container 14, and is provided with opposite detents 20 (only one shown in FIG. 1) for retaining a spare cap in place.

The specimen transporting and processing system 10 is composed of several elements. First is a tubular container 22 having an open end 24 which is threaded at 26. An annular collar 28 is secured thereto, having a female thread 30 applied on the thread 26. The collar 28 also has an upstanding annular portion having a male thread 32 which engages a female thread 34 of a removable cap 36. As illustrated, both the cap 36 and the collar 28, on their exterior surfaces, can be fluted or otherwise roughened to provide a better grip for the user.

The collar 32 includes an internal annular protrusion 38 shaped to engage a groove 40 of a filter assembly 42. As its name implies, the filter assembly 42 is used for filtering, and therefore is provided with a series of holes or perforations 44 for the passage of liquid therethrough.

Figure 2:
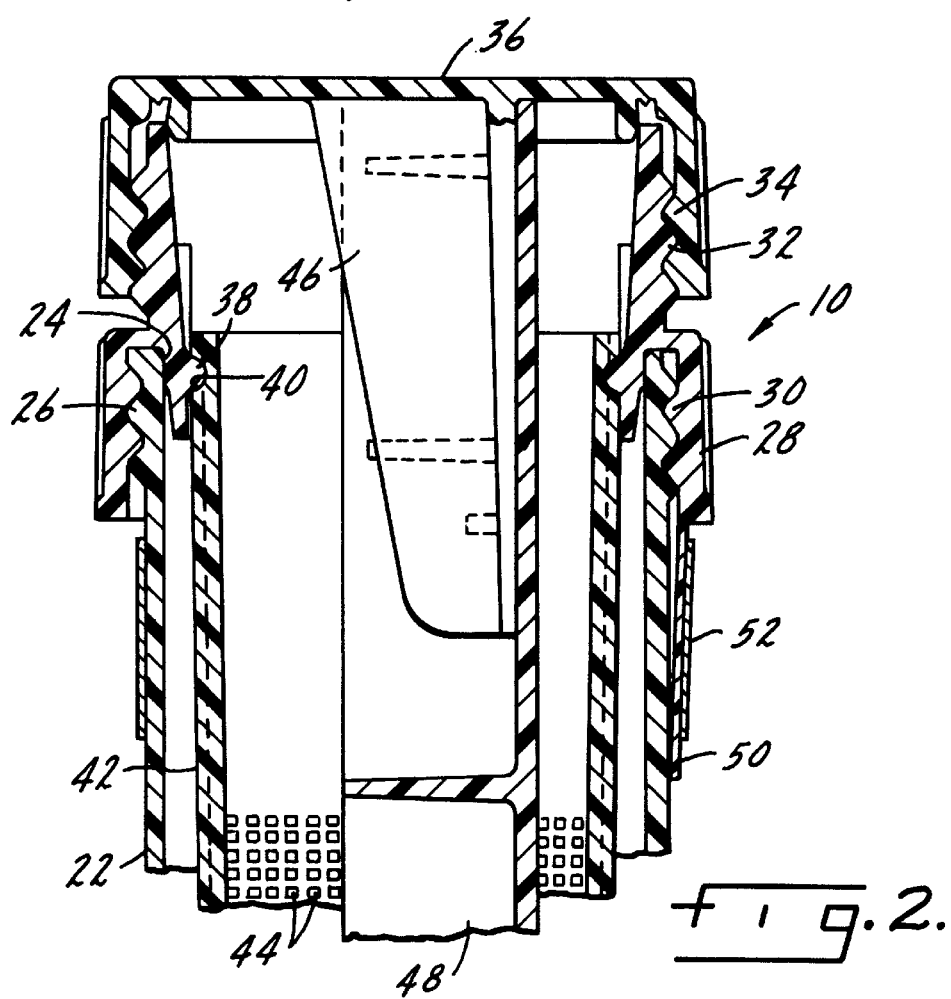
FIG. 2 is an enlarged cross-sectional view through the top portion of the right hand container of FIG. 1, illustrating details of the assembly and showing the tape strip and tab for securing the removable collar in place.

The cap 36 has an integral support 46 extending downwardly from the underside of the cap 36. A specimen sampling implement 48 is secured to the support 46 by appropriate means, such as by force fitting, an adhesive, sonic welding, heat staking, or otherwise. While not illustrated in the drawing figures, the sampling implement 48 may be terminated with a spoon-like end or otherwise for sampling purposes. It is shaped to fit within the filter assembly 42 when the system 10 is assembled as illustrated in FIGS. 1 and 2.

The cap 36 is threadedly secured to the upper portion of the collar 28 and the collar 28 is, in turn, threadedly secured to the open end of the container 22. The system 10 is normally utilized by both a patient and a diagnostician, where the patient removes the cap 36, collects a sample with the implement 48, and then inserts the sample into the container 22 by applying the cap 36 to the collar 28. The sample can then be mixed with an appropriate reagent (not illustrated) in the container 22, and can be further handled by the diagnostician as required.

While it is intended that the patient only remove the cap 36, occasionally when the patient attempts to remove the cap 36, the collar 28 will inadvertently unscrew from the open end 24 of the container 22. To prevent premature and inadvertent rotation of the collar 28, the collar 28 is provided with an extending tab 50 adjacent to the container 22. The tab 50 preferably is shaped with approximately the same curvature of the container 22 so as to lie close to the exterior surface of the container 22.

The tab 50 is bound to the container 22 by means of a tape strip 52 which adheres to both the tab 50 and the container 22. Preferably, as illustrated, the tape strip 52 extends around the entire periphery of the container 22. While not illustrated in the drawing figures, the tape strip 22 can be provided with appropriate printed indicia thereon to warn the patient not to remove it, such as "For Lab Use Only", or a similar warning. Thus, with the tape strip 52 adhering to both the tab 50 and the container 22, the collar 28 is locked in place, and when the patient seeks to remove the cap 36, only the cap 36 will rotate while the collar 28 remains in place. Only after the tape strip 52 is broken or removed can the collar 28 be rotated, and therefore inadvertent rotation of the collar 28 will not occur.

While it is preferred that the tape strip 52 be provided in combination with the extending tab 50 to securely lock the collar 28 in place, other means of doing so are also possible. For example, a releasable adhesive can be applied to the underside of the tab 50 between the tab 50 and the container 22 to temporarily lock the collar 28 in place. The tab 50 could then be lifted or simply sufficient rotational force applied to the collar 28 when its removal is desired to break the adhesion between the tab 50 and the container 22. Other means of temporarily securing the tab 50 to the container 22 will also become apparent given the nature of the temporary locking described above. Such other means can comprise a temporary heat stake or sonic weld of the tab 50, or locking protrusions on the outside surface of the container 22 to temporarily capture the tab 50 until it is desired that the collar 28 be unscrewed. In addition, more then one tab 50 can be employed, if desired, although normally only a single tab is necessary, in combination with the applied tape strip.

In combination with the system 10, the second container 14 can also be used for specimen collection, as explained in greater detail in incorporated U.S. Pat. No. 5,431,884. The containers 14 and 22 can be employed to collect specimens for the same diagnostic processes, or different processes, as needs dictate.

Various changes can be made to the invention without departing from the spirit thereof or scope of the following claims.

What is claimed is:

1. A specimen transporting and processing system, comprising
   a. a tubular container having an open end,
   b. a removable collar attached to said container at said open end, said collar being threadedly secured to said open end,
   c. means secured to said collar for sealing said container at said open end, and
   d. means for temporarily locking said collar on said open end when threadedly secured thereto, said locking means comprising,
      i. at least one tab secured to said collar and extending from said collar adjacent an outer surface of said container, and
      ii. adhesive means temporarily securing said tab to said outer surface such that said tab is immobile and connected to said outer surface until connection is breached.

2. A specimen transporting and processing system according to claim 1 in which said adhesive means temporarily securing comprises a tape strip adhesively adhering to said tab and said outer surface.

3. A specimen transporting and processing system according to claim 2 in which said tape strip extends around said container.

4. A specimen transporting and processing system according to claim 1 including a tubular filter shaped to fit within said container through said open end, said collar having means for gripping said filter.

5. A specimen transporting and processing system according to claim 4 in which said gripping means comprises an internal annular protrusion in said collar, and in which said filter includes an annular groove shaped to engage said protrusion.

6. A specimen transporting and processing system according to claim 1 in which said sealing means comprises a cap.

7. A specimen transporting and processing system according to claim 6 including a specimen sampling implement secured to said cap and shaped to be inserted into said container.

8. In a container for transporting substances, the container being tubular and having a removable collar threadedly secured to an open end of the container and having a cap threadedly secured to the collar for sealing the container at the open end, the improvement comprising means for preventing rotation of said collar on said open end when said cap is rotated, said means for preventing rotation comprising
   a. at least one tab secured to said collar and extending from said collar adjacent an outer surface of said container, and
   b. adhesive means temporarily securing said tab to said outer surface such that said tab is immobile and connected to said outer surface until connection is breached.

9. A container according to claim 8 in which said adhesive means temporarily securing comprises a tape strip adhesively adhering to said tab and said outer surface.

10. A container according to claim 9 in which said tape strip extends around said container.

* * * * *